(12) United States Patent
Li et al.

(10) Patent No.: US 9,645,057 B2
(45) Date of Patent: May 9, 2017

(54) METHOD FOR IMPROVING ANALYSIS OF MICROORGANISMS IN COMPLEX MATRICES

(71) Applicant: Becton, Dickinson and Company, Franklin Lakes, NJ (US)

(72) Inventors: Xiao Li, Germantown, MD (US); Kenneth Anthony Kopher, Baltimore, MD (US); John D. Mantlo, Westminster, MD (US); William Alfred Pope, Owings Mills, MD (US); Song Shi, Reistertown, MD (US); Axel A. Yup, Owings Mills, MD (US)

(73) Assignee: Becton, Dickiinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/774,392

(22) PCT Filed: Apr. 4, 2013

(86) PCT No.: PCT/US2013/035263
§ 371 (c)(1),
(2) Date: Sep. 10, 2015

(87) PCT Pub. No.: WO2014/143077
PCT Pub. Date: Sep. 18, 2014

(65) Prior Publication Data
US 2016/0011087 A1 Jan. 14, 2016

Related U.S. Application Data

(60) Provisional application No. 61/779,766, filed on Mar. 13, 2013.

(51) Int. Cl.
*C12Q 1/68* (2006.01)
*G01N 1/30* (2006.01)
*C12Q 1/06* (2006.01)
*C12Q 1/04* (2006.01)

(52) U.S. Cl.
CPC ............... *G01N 1/30* (2013.01); *C12Q 1/04* (2013.01); *C12Q 1/06* (2013.01); *G01N 2001/302* (2013.01)

(58) Field of Classification Search
None
See application file for complete search history.

(56) References Cited

U.S. PATENT DOCUMENTS

| 8,889,349 B2 | 11/2014 | Takenaka et al. |
| 2003/0228651 A1 | 12/2003 | Votaw et al. |
| 2010/0129813 A1 | 5/2010 | Levin |
| 2011/0217694 A1 | 9/2011 | Buzatu et al. |

FOREIGN PATENT DOCUMENTS

| CN | 101713713 A | 5/2010 |
| EP | 0915171 A2 | 5/1999 |
| JP | 2011092104 A | 5/2011 |
| WO | 2005010528 A1 | 2/2005 |
| WO | 2010019960 A2 | 2/2010 |
| WO | 2013152203 A1 | 10/2013 |

OTHER PUBLICATIONS

International Search Report and Written Opinion for Application No. PCT/US2013/035263 dated Oct. 8, 2013.
Dwivedi et al., "Detection of pathogens in foods: the current state-of-the-art and future directions", Critical Reviews in Microbiology , vol. 37, No. 1, pp. 40-63 (2011 ).
Stevens et al., "Bacterial separation and concentration from complex sample matrices: a review", Critical Reviews in Microbiology, vol. 30, No. 1, pp. 7-24 (2004).
McHugh et al., "Flow cytometry for the rapid detection of bacteria in cell culture production medium", Cytometry Part A, vol. 71A, No. 12, pp. 1019-1026 (2007).
Breeuwer et al., "Characterization of uptake and hydrolysis of fluorescein diacetate and carboxyfluorescein diacetate by intracellular esterases in Saccharomyces cerevisiae, which result in accumulation of fluorescent product", Applied and Environmental Micriobioly, 61 (4) : 1614-1619 (Apr. 1995).
de Boer et al., "Methology for detection and typing of foodborne microorganisms", International Journal of Food Microbiology, 50(1-2) : 119-130 (Sep. 1999).
Quintero-Betancourt et al., "Cryptosporidium parvum and Cyclospora cayetanensis: a review of laboratory methods for detection of the waterborne parasites", Journal of Microbiological Methods, 49(3) : 209-224 (May 2002).
Hammes, F. et al., "Cytometric methods for measuring bacteria in water: advantages, pitfalls, and applications", Anal. Bioanal. Chem., vol. 397, pp. 1083-1095 (2010).
Gunasekera, et al. "A Flow Cytometry Method for Rapid Detection aqnd Enumeration of Total Bacteria in Milk," Applied and Environmental Microbiology, vol. 66, No. 3, Mar. 2000, p. 1228-1232.
Thomas J-C et al: "Quantitative Flow Cytometric Detection of Specific Microorganisms in Soil Samples Using RRNA Targeted Fluorescent Probes and Ethidium Bromide", Cytometry, Alan Liss, New York, US, vol. 27, No. 3, Jan. 1, 1997 (Jan. 1, 1997), pp. 224-232, XP009014220, ISSN: 0196-4763, DOI: 10.1002/ (SICI)1097-0320 (Mar. 1, 1997) 27:3<224: :AID-CYT03>3.0. C0;2-E * p. 226, left-hand column, paragraph 2 *.
Laplace-Builhe C et al: "Application of flow cytometry to rapid microbial analysis in food and drinks industries", Biology of the Cell. Elsevier, Paris, FR, vol. 78. No. 1-2, Jan. 1, 1993(Jan. 1, 1993), pp. 123-128, KP023598976, ISSN: 0248-4900, DOI:10.1016/0248-4900(93)90122-U [retrieved on Jan. 1, 1993] * abstract *.

(Continued)

*Primary Examiner* — James Martinell
(74) *Attorney, Agent, or Firm* — Lerner, David, Littenberg, Krumholz & Mentlik, LLP

(57) ABSTRACT

A process for determining one of the presence, absence, or total of microorganisms (e.g. bacteria) in a sample. According to the process, a biological sample containing complex matrices is obtained. The sample is first combined with a resin to adsorb complex matrices from the sample. The resin is removed from the biological sample. The sample so prepared is then analyzed by flow cytometry.

22 Claims, 4 Drawing Sheets

(56) References Cited

OTHER PUBLICATIONS

Alvarez-Barrientos A et al: "Applications 1-15 of flow cytometry to clinical microbiology", Clinical Microbiology Reviews, Washington, DC, US, vol. 13, No. 2, Apr. 1, 2000 (Apr. 1, 2000), pp. 167-195, XP002218122, ISSN: 0893-8512, DOI:10.1128/CMR.13. 2.167-195.2000 * p. 169, right-hand column, paragraph 2*.
Mosiman V L et al: "Reducing Cellular Autofluorescence in Flow Cytometry: An in Situ Method", Cytometry, Alan Liss, New York, US, vol. 30, Jan. 1, 1997 (Jan. 1, 1997), pp. 151-156, XP002909760, ISSN: 0196-4763, DOI: 10.1002/(SICI)1097-0320(19970615) 30:3<151: :AID-CYT06>3.0.00;2-0 * abstract *.
European Search Report for EP Application No. 13878493.9 dated Oct. 5, 2016.

METHOD FOR IMPROVING ANALYSIS OF MICROORGANISMS IN COMPLEX MATRICES

CROSS REFERENCE TO RELATED APPLICATIONS

The present application is a national phase entry under 35 U.S.C. §371 of International Application No. PCT/US2013/035263 filed Apr. 4, 2013, published in English, which claims priority from U.S. Provisional Patent Application No. 61/779,766 filed Mar. 13, 2013, and is related to U.S. Provisional Application No. 61/620,823 filed on Apr. 5, 2012, all of which are hereby incorporated herein by reference.

BACKGROUND OF THE INVENTION

Determining the identity and total number of viable organisms in a particular sample is of tremendous importance. Of specific importance is monitoring and ensuring the safety of food and water supplies through the surveillance and identification of pathogenic organisms in foods and in the environment quickly, efficiently, and accurately.

One such method to accomplish this is the total viability organism (TVO) assay. The TVO assay is widely used today as a quality control application in the industrial microbiology field. The TVO assay is used, for example, to monitor the number and types of bacteria in consumer food products, such as meat. The TVO method can also be used to monitor bacterial populations in drinking water. Monitoring for food and water is, of course, critical to ensure that the food and water supply is safe for consumption.

The steps of the TVO assay generally include: 1) obtaining a test sample; and 2) culturing or plating the sample on agar (a gelatinous nutrient substance), placed in a suitable container. The microbial organisms are allowed to grow and the colony forming units (CFUs) are calculated based on the number of colonies that form on the agar. CFUs can be calculated only after allowing time for colony growth. Samples are typically diluted and this dilution factor (i.e., volume ratio of sample to total volume) is taken into account when calculating CFUs.

Samples can also be cultured on a variety of agar plates that contain different types of selective media to help isolate target microorganisms and more accurately and reliably determine what types of microorganisms are present. Selective agents (e.g., antibiotics, anti-fungals, etc.) will eliminate certain non-target microorganisms (e.g., bacteria of no interest). This avoids the possibility of spurious results that might occur if colonies from many different types of microorganisms are formed.

Selective agents can also favor the growth of certain types of microorganisms over others. Although the TVO assay allows for detection of different microorganism species, e.g., different bacterial species, food and environmental microbiologists must often choose between enumeration and identification without the option of both. Although selective agents can be added to favor the growth of a specific group of organisms, the TVO assay is often based on the ability of normal healthy cells to multiply in nutrient-rich medium (i.e., without selection). TVO therefore has the capacity to measure the total number of microorganisms or a group of microorganisms in the sample tested. However, because of the lack of ability to differentiate specific microorganisms, TVO can be relatively nonspecific for the microorganism population as a whole.

There are numerous other methods available that identify specific microorganisms, especially pathogens. Such methods are widely used in the clinical setting. Methods for detecting microorganisms often depend upon enrichment of the microorganism culture in order to increase the numbers of the target microorganism and to allow for the resuscitation of injured microorganisms. When selective and differential plating is employed, researchers are able to discriminate the target organism from the background microflora. However, the results are almost always non-enumerative. In other words, only the presence or absence of a particular bacterial population can be determined, not the quantity.

Utilizing both sample enrichment and selective plating results is a time-consuming assay, which often takes several days before even a preliminary result can be obtained. Although such enrichment and selective plating is a staple procedure to determine the number and types of microorganisms in a sample, it can typically take several days to get a final result after colonies grown on agar are counted. The amount of time it takes to obtain results is the most significant drawback of using the staple TVO assay.

Different methods have been developed that attempt to shorten detection time by eliminating the selective and differential plating steps. Such methods include DNA hybridization, agglutination, and enzyme immunoassay. Although these alternative techniques have shortened the time for detection, culture enrichment steps remain necessary because these methods only allow for the ultimate detection of $10^3$-$10^4$ CFU of the target pathogen. Therefore, confirmation for presumptively positive results remains necessary for the TVO assay.

Furthermore, there is no universal method or single technique available for analyzing a biological sample, especially a food sample, to detect for the presence or absence of multiple microorganisms. This makes the sample preparation steps for the separation and subsequent concentration of microorganisms from a biological sample prior to assay for the microorganisms a rate limiting step in molecular methods for the detection of pathogens, including foodborne pathogens.

With regard to specific sample preparation techniques for separation of microorganisms, techniques that utilize centrifugation followed by washing and filtration steps are not advantageous because they result in a significant loss of, or damage to, microorganisms during the processing. Furthermore, the whole procedure is not amenable for automation.

In order to achieve separation of the microorganism from the sample, affinity agents for a particular microorganism have been employed. However, affinity agents used to isolate microorganisms from the complex matrices are also complicated to deploy because of: 1) lack of universal affinity agents that bind to all organisms selectively from the other sample constituents; 2) variability in binding affinities of different organisms to the universal affinity reagents; and 3) difficulty in eluting the bound organism back into the solution.

Other techniques for identifying pathogens in food and water are also known. For example, flow cytometry has been reported as a rapid technique for enumerating and identifying microorganisms. Flow cytometry is a method originally used to separate and analyze eukaryotic cell populations but has been employed in the evaluation and detection of microorganisms, as well. Specifically, microorganisms that have been fluorescently stained are passed through a beam of light. A pattern unique to the microorganism of interest is achieved by the combination of both the adsorption and scattering of the light. (Breeuwer et al., Characterization of uptake and hydrolysis of fluorescein diacetate and carboxy-fluorescein diacetate by intracellular esterases in *S. cerevisiae*, which result in accumulation of fluorescent product, *Appl. Environ. Micriobiol.*, 61(4):1614-9 (April 1995); de Boer & Beumer, Methodology for detection and typing of foodborne microorganisms, *Int. J. Food. Microbiol.*, 50(1-2):119-30 (September 1999)).

The main advantage of flow cytometry is that it is fast and easy to perform. Flow cytometry is adaptable to different types of samples and methods, making it a robust application that is also amenable to automation. It is no surprise that numerous flow cytometry applications have emerged in industrial biotechnology, food and pharmaceutical quality control, routine monitoring of drinking water and wastewater systems, and microbial ecological research in soils and natural aquatic habitats. Flow cytometry results correlate well with the results of standard plate counting methods. However, flow cytometry has other limitations, such as the need to dye label target microorganisms for detection, the high cost of the equipment and the need for specialized training of personnel. The extensive and routine use of this technique has begun to alleviate these drawbacks.

However, other practical problems remain with flow cytometry, especially in the context of analyzing biological or environmental samples derived from what are referred to as "complex matrices." Complex matrices may consist of substances that interfere with the detection of microorganisms in the biological or environmental sample. Further limits on detection are imposed by interference of nonspecific fluorescence or by particulate matter, less than optimal detection limits, difficulty in applying the method to solid or particulate food samples, the inability to differentiate between viable and dead cells unless specialized staining is used, and destruction of cellular viability that may also occur during sample processing (Quintero-Betancourt et al., *Cryptosporidium parvum* and *Cyclospora cayetanensis*: a review of laboratory methods for detection of the waterborne parasites, *J. Microbiol. Methods*, 49(3):209-24 (May 2002)).

The presence of interfering substances or particulate matter in the sample increases the background noise and complicates analysis of biological or environmental samples using flow cytometry. With these drawbacks in mind, many researchers have been reluctant to fully explore the use of flow cytometry for analyzing samples, especially those containing particulates, as they have considered it not very promising for routine use.

Because of the cell wall structures and the permeation properties of fluorescent dyes, agents such as EDTA sometimes are required in the staining solution to destabilize the outer membrane of Gram negative bacteria cells and increase dye uptake. The staining intensities of some Gram negative bacteria in complex matrices, such as ground beef extract, are not as high as the staining intensity of bacteria in buffer or buffer containing low amount of complex matrices, and the addition of EDTA is not able to address the problem of low staining intensity with these types of samples. As a result, the stained population of certain organisms is very close to the background and the low signal to background ratio will ultimately have an impact on counting accuracy and sensitivity.

Consequently, methods that address the drawbacks in current methods for detecting the presence or absence of microorganisms in a sample using flow cytometry are sought.

SUMMARY OF THE INVENTION

The present invention relates to a method of identifying the presence or absence of at least one microorganism in a sample. As described herein, a biological or environmental sample to be tested for the presence or absence of at least one microorganism is first obtained, and then prepared for the assay to be performed. The prepared sample is combined with a resin, after which the resin is removed from the sample. The prepared sample is then combined with labels for the assay target, after which the sample is analyzed to determine the presence or absence of the assay target.

In one embodiment of the invention, the sample to be analyzed is obtained from a biological or environmental sample that is or contains a complex matrix. Complex matrices are found in a variety of samples including, but not limited to, food products, cosmetics, and soil samples. The sample to be analyzed may be prepared using known techniques for that particular type of biological or environmental sample prior to the introduction of the resin and well known to the skilled artisan.

In another embodiment of the invention, resins are used to modulate or reduce the interference of the complex matrices with downstream sample assay analysis. Various resins are known in the art and selection of a particular resin or resins will depend on the nature of the biological or environmental sample to be analyzed. The resin can be removed prior to performing the assay by techniques such as filtration, but the particular technique employed is largely a matter of design choice and depends upon the type of resin and sample preparation. The skilled person will select a suitable separation technique based upon these and other factors.

In another embodiment, the sample, after resin treatment and removal of resin, is analyzed using a flow cytometer. An appropriate dye, such as a nucleic acid dye or other fluorescent dye, is combined with the sample after removal of resin and prior to flow cytometry. The dye facilitates the detection of the assay target in the flow cytometer. Enhancing techniques, such as quenching, may also be employed to further improve the integrity of the assay.

DETAILED DESCRIPTION

Figure 1:
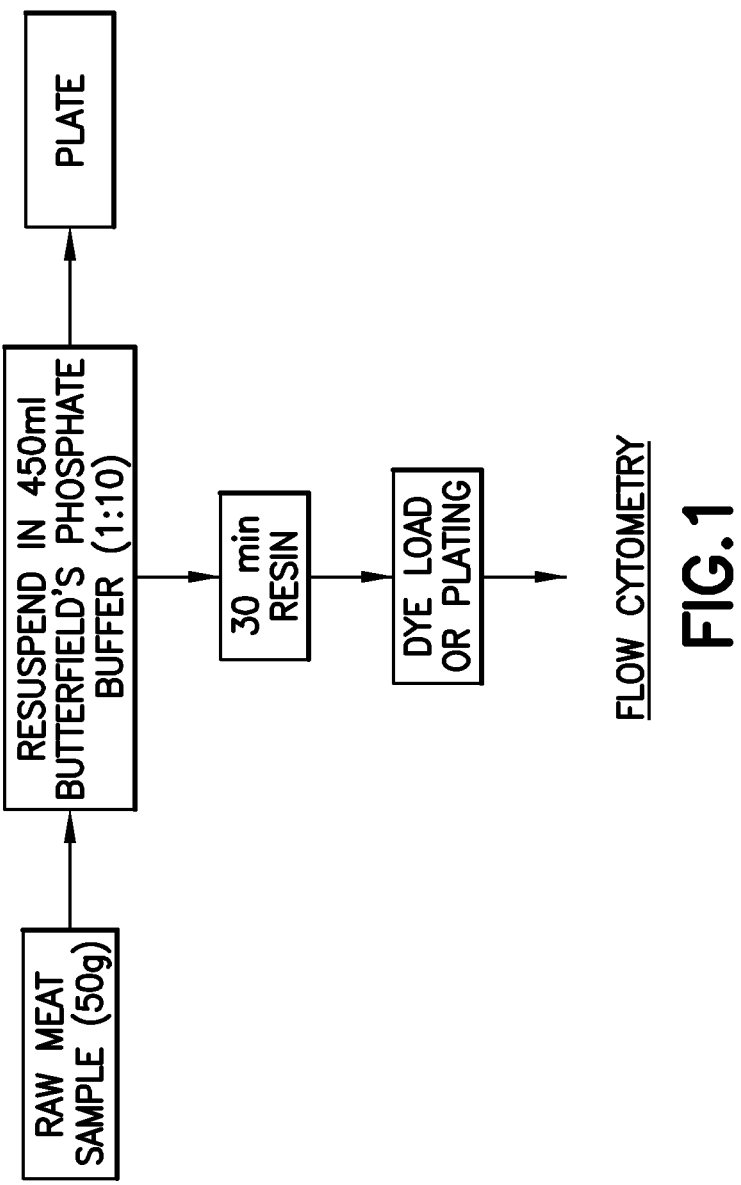
FIG. 1 illustrates the steps of one embodiment of the method described herein for detecting bacteria in a biological sample using flow cytometry.

Accurate determination of live, dead, and total bacteria is important in many microbiology applications. For culture based methodologies, viable microorganisms that will form colonies on solid growth medium and proliferate in liquid nutrient broths are required. These traditional, culture-based tests are time-consuming and can work poorly with viable microorganisms that are either slow-growing or non-culturable. As such, these traditional, culture-based tests do not provide real-time results or timely information that is needed in applications such as health-related monitoring of food and water for the presence of pathogens.

Disclosed herein are methods for improving upon known assays, such as the TVO assay, by deploying flow cytometry for biological samples obtained from complex matrices. Biological samples obtained from or containing complex matrices, such as food products, cosmetics, and soil samples, can be difficult to accurately analyze using flow cytometry because of the interference caused by the particles of the complex matrix. More specifically, the complex matrices make it difficult to optically detect the target microorganisms in the sample, because it remains difficult to differentiate the target microorganisms from the other sample constituents.

Specifically, the methods described herein separate microorganisms in a sample from other sample constituents that are commonly described as complex matrices (e.g., ground beef, eggs, milk, soil, cosmetics, etc.) and enhance sample quality prior to subjecting the sample suspected of containing target microorganisms to tests or assays for the detection of the presence or absence of target microorganisms. Advantages of using the methods described herein include, but are not limited to, facilitating the detection of multiple microorganism strains; removing matrix-associated assay inhibitors; removing interfering matrix particulates; enhancing the strength or ability to read the detection signal and providing adequate sample size reduction to allow for the use of representative food sample sizes and/or small media volumes.

The methods described herein aid in improving sample preparation in a manner necessary to detect low levels of pathogens or sporadic contamination, which may perhaps reduce or even eliminate the need to enrich the sample culture prior to detection in order to accelerate microorganism growth.

The methods described herein concentrate the target microorganisms/pathogens/bacteria in the sample (if present) by removing matrix-associated inhibitors from the sample that may interfere with the assay for the target microorganisms/pathogens/bacteria, while also enhancing detectable signal obtained from the sample that is indicative of the presence or absence of the target microorganisms/pathogens/bacteria. The method is advantageous in that it is also universal (e.g., applicable to multiple types of matrices and target microorganisms/pathogens/bacteria), and is simple, rapid, and inexpensive. Furthermore, the method described herein reduces the chance for false positive or negative results that might occur because of cross-reactivity of the target microorganisms/pathogens/bacteria with residual matrix components or because of the detection of dead target cells.

The methods described herein introduce resins into the sample combined with complex matrices to modulate or reduce the interference of the complex matrices with downstream sample assay analysis. The resins or combinations of resins adsorb residual matrix components, and the separation of the resins from the sample in turn remove the complex matrices from the sample. It is to be understood that, throughout this application, the adsorption by the resins refers to the ability of the resins to modulate, or reduce, or eliminate signal detection interference from complex matrices without adversely affecting the viability of the microorganisms within the matrix. As described in greater detail herein, downstream assays to detect the presence or absence of microorganisms/pathogens/bacteria in the sample typically require that the target be viable for reliable detection. The physical effect of the resins on other sample constituents that may be present in the matrix is not important so long as the resins do not have significant adverse impact on target microorganism viability.

More particularly, the resins, which may be used in the practice of the methods described herein, include non-functional polymeric resin adsorbents. The resins have recesses/irregular surfaces referred to herein as pores. Non-functional polymeric resin, as used herein, is polymeric resin that does not possess moieties or functional groups that may significantly react with sample constituents.

In another embodiment, non-functional resins, such as the XAD resins manufactured by Rohm & Haas, particularly XAD-4 resin, which is a non-functional copolymer of styrene and divinyl benzene, may be used in the practice of the described methods.

It should be understood that the resin pore size is not critical to the practice of the methods described herein. Generally, resins do not have a pore size large enough to permit bacteria to penetrate into the interior of the resin. Certain resins, however, have macroporous structures with large internal surfaces which permit large molecules to penetrate into their interiors. Such macroporous resins are entirely suitable for use in the practice of the present invention since entrapment of the bacteria within the pores does not necessarily adversely affect the viability of the microorganism. To the extent that macroporous resins trap bacteria, the skilled person will be able to determine if the degree of entrapment adversely affects the downstream analysis of the sample. Resins which have relatively smaller pores wherein adsorption is affected principally on the external surfaces of the resin, that is, microporous resins are also suitable in the practice of the invention.

A particularly preferred resin is a non-functional polymeric absorbent resin, such as XAD-4. Such a resin removes interfering matrix components from the sample, while not adversely affecting the viability of microorganisms contained in the biological sample. Based upon the guidance provided herein, the skilled person will be able to select other suitable hydrophobic porous resins for use in the methods described herein.

After the sample is treated with the resin, the resin, with complex matrices adsorbed thereon, is separated from the sample. Separation of the target microorganism from the complex matrices prior to staining is advantageous because the staining intensities of some Gram negative bacteria in complex matrices, such as ground beef extract, are not as high as the staining intensity of bacteria in buffer or buffer containing low amount of complex matrices, and the addition of EDTA, which increases dye uptake, is not in and of itself able to resolve this issue.

The sample is then stained for the assay to detect the presence or absence of one or more target microorganisms in the sample. The isolated, concentrated, and stained biological sample is then analyzed for the presence or absence of target microorganisms using flow cytometry.

The disclosed method contemplates obtaining a biological sample. The biological or environmental sample may be in the form of a complex matrix, such as food, soil, cosmetics, etc. Suitable samples are in liquid form.

The biological or environmental sample is prepared for analysis as discussed generally above and in FIG. 1. Sample preparation will depend upon the nature of the sample. Sample preparation of biological or environmental samples for analysis are well known to those skilled in the art and therefore not described in detail herein. In one exemplary embodiment, the meat is first blended with a buffer. The use of a standard protocol for blending meat with the proper buffer to obtain the meat extract is contemplated as suitable for use in the methods described herein. Blending is accomplished using a variety of techniques, such as adding the meat sample to the appropriate volume of phosphate buffered dilution water and transferring to a stomacher bag (<50 µM filter—Interscience Bag system: 111625 or equivalent) and blended in a stomacher for (e.g., Tekmar (Seward) Stomacher Lab Blender 400 or equivalent). Such protocols are well known to those skilled in the art and are not described in detail herein. Examples of such protocols are described on the USDA website (http://www.fsis.usda.gov/OPHS/microiab/mIgchp3.pdf), which is incorporated by reference herein.

The proper amount of prepared sample is then transferred to a sterile container, such as a test tube, that either contains a resin or to which resin is added. The skilled person will be able to determine the amount of resin to be added to a sample. Care must be taken so that enough resin is added to remove debris from the sample but not adversely affect the viability of the microorganisms in the sample for downstream testing. Specifically, the prepared biological sample is treated/incubated with a resin that may potentially bind/interact with substances (e.g., constituents of the complex matrices) that interfere with the analysis of the biological sample using flow cytometry.

In one embodiment, the prepared biological samples are treated at room temperature with resin for less than one (1) hour. Preferably, the prepared biological samples are treated with resin for less for thirty (30) minutes or less by rotating the resin-treated sample at 25 rpm. In another embodiment, the resin is a non-functional nonionic adsorbent resins.

After the prescribed time period, the resin is separated from the prepared biological sample taking with it complex matrices adsorbed by the resin.

In another embodiment, the resin is removed or otherwise separated from the biological or environmental sample by filtration or by allowing the resin to settle and removing the supernatant from the vessel in which the resin has settled.

After the resin is removed from the prepared biological sample, the remaining sample constituents are combined with a stain for detection of the target microorganism(s). One example of a stain is a molecular label. In a further exemplary embodiment, the molecular labels are fluorescent dyes or stains. Such stains are well known to one skilled in the art. Therefore, such stains, and how they are deployed, are not described in detail herein. However suitable staining protocols are described in U.S. Provisional Application No. 61/620,823 filed on Apr. 5, 2012 which is commonly owned with the present application and is incorporated by reference herein.

In a further embodiment, staining can be accomplished by using nucleic acid dye stain (e.g., SYTO® 13 by Invitrogen). When selecting a stain, the skilled person will consider the following factors: i) the target microorganism of interest (e.g. gram positive or gram negative), the downstream assay being deployed for determining the presence or absence of the microorganism in the sample; and iii) the contrast between the selected stain and other stains for sample constituents. The skilled person is aware of other considerations when selecting a dye stain for the method described herein.

As described above, fluorescent nucleic acid dyes permeable to both live and dead organisms are used to label cells in suspension for flow cytometry studies. However, detection sensitivity of such flow cytometry studies can be impacted while the targeted cells are in a suspension with the particles that bind to the nucleic acid dyes non-specifically.

Several approaches are described herein to remove and mask the fluorescent signals from those interfering particles from the solution and subsequently increase detection sensitivity.

As described in U.S. Provisional Application No. 61/620,823, in one embodiment, excess amount of background signal-reducing molecules that do not permeate viable cells but have similar binding properties as the nucleic acid stains are added sequentially or simultaneously with the cell permeable nucleic acid stain to the sample of interest. Since the background signal-reducing molecule is not permeable to the viable cells, only the cell permeable nucleic acid dye can label the viable cells and generate fluorescent signals from the cells. Interfering particles that bind to the dye non-specifically and dead cells with permeable cell membrane are bound to both the nucleic acid stain and the background signal-reducing background signal-reducing molecule described above. The background signal-reducing molecule competes with the nucleic acid stain to bind to the extra cellular particles and dead cells. As a result, there is a reduced intensity of fluorescent signal caused by the non-specific binding of the nucleic acid stains to the non-target particles when samples are analyzed by flow cytometry. The presence of the background signal-reducing molecule reduces the intensity of the background signal caused by the non-specific binding of the nucleic acid stain to non-target particles that remain in the sample after the resin has extracted some of these particles from the sample.

In another embodiment, the staining process can also be done in conjunction with a quenching protocol. For example, prior to completing the staining with nucleic acid dye, a quencher, such as nitrazine yellow, can be added during the staining process to help differentiate the detection signal for the target microorganism from the background signal. Such signal quenching thereby enhances contrast by decreasing the fluorescence intensity of unwanted signal. Quenchers accomplish this by absorption of dye fluorescence that would otherwise generate spurious signals.

The methods described herein also contemplate quenching the background signal described above. As described in U.S. Provisional Application No. 61/620,823, in one embodiment, the nucleic acid binding domain of the dye or the total dye molecule is covalently linked to one or more fluorescent quenchers that do not permeate viable cells that can quench the fluorescent signal of the nucleic acid dye by spectra overlap. Such molecules can be added sequentially or simultaneously with the cell permeable nucleic acid stain to the sample of interest. Since the molecule is not permeable to the viable cells, only the cell permeable nucleic acid dye can label the viable cells and generate fluorescent signals. Non-target particles, such as e.g., dead cells with permeable cell membrane and interfering particles that bind to the dye nonspecifically bind to both the nucleic acid stain and the linked quencher. The molecule linked to quencher competes with the nucleic acid stains with binding sites on the non-target particles. The quencher will reduce the fluorescent intensity of the signals emitted by the nucleic acid stains bound to the non-target particles (if the quenchers are sufficiently proximate to the nucleic acid stains bound to the non-target particles).

The prepared biological sample, after removal of the resin and molecular labeling of target viable microorganism in the sample, is then analyzed. In one embodiment, the analysis is done using a flow cytometer. The use of flow cytometry is well known to those skilled in the art, and not described herein. A description of flow cytometry analysis is described in Hammes, F. et al., "Cytometric methods for measuring bacteria in water: advantages, pitfalls, and applications,"

Anal. Bioanal. Chem., Vol. 397, pp. 1083-1095 (2010), which is incorporated herein by reference. The whole process can be automated as well. The described method adapts flow cytometry to detect pathogens in samples with complex matrices.

The following examples are provided to further illustrate certain embodiments of the invention. As such, the examples are not limiting in terms of materials, compositions and conditions used. Other suitable modifications and adaption of the variety of conditions and parameters normally encountered and that are obvious to those skilled in the art are within the spirit and scope of the invention described herein.

EXAMPLES

Example 1

FIG. 1 generally illustrates the steps involved in preparing and testing meat samples. These steps are discussed in more detail below.

Resin Preparation

Resin was prepared by weighing 50 g of XAD-4 resin and washing with 100 mL denatured ethanol by shaking at 240 rpm for 30 minutes at room temperature.

After ethanol wash, the resin was allowed to settle and ethanol was decanted. The resin was then suspended in 250 mL deionized water and placed in a shaker for 30 minutes at 240 rpm and at room temperature. The resin was allowed to settle after shaking and the deionized water was decanted. This process was repeated 3 or 4 times.

The resin was then suspended in 250 ml deionized water and sterilized by autoclaving at 121° C. for 30 minutes. Optionally, the resin may be stored at 2 to 8° C. until needed.

Sample Preparation

Ground beef (25 grams) was spiked with a microorganism of interest (e.g., *E. coli* ATTC NO. 25922, *S. typhimurium* ATTC NO. 14028, *P. aeruginosa* ATTC NO. 27853, *P. aeruginosa* ATTC NO. 9027, *S. auerus* ATTC NO. 25923, *S. epidermidis* ATTC NO. 12228 or *L. monocytogenes* ATTC NO. 13932) resulting in a bacterial load of $1 \times 10^6$ microorganisms per gram of ground beef.

Spiked ground beef (25 grams) was added to 200 mL of Phosphate Buffer pH 7.2 (BD Diagnostics Bottled Media BD-214973 or equivalent), transferred to a stomacher bag (<50 μM filter—Interscience Bag system: 111625 or equivalent) and blended in a stomacher (e.g., Tekmar (Seward) Stomacher Lab Blender 400 or equivalent) for 2 minutes.

Figure 4:
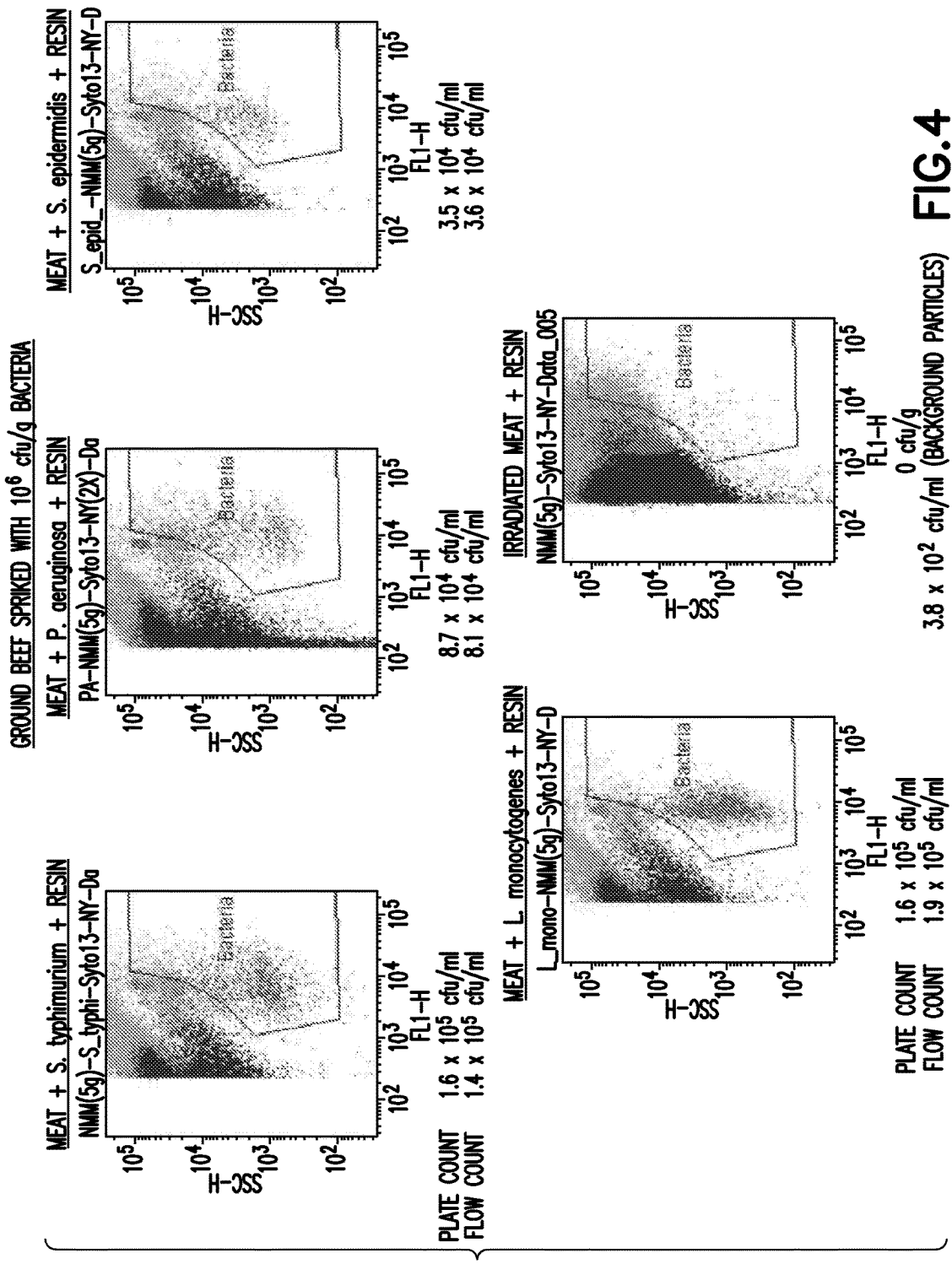
FIG. 4 presents a series of dot plots generated during flow cytometric analysis to determine the amount of bacteria in spiked ground beef and comparing the results to results obtained from a TVO assay.

The stomached liquid was filtered through a 40 μm strainer (Becton Dickinson Falcon 352340 or equivalent) to create ground beef extract. Some of the ground beef extract was used for the TVO assay by plating on agar using known techniques. The TVO assay was done as a comparison to the flow cytometry results. (See FIG. 4).

Sample Treatment with Resin

Prepared XAD-4 resin (5 grams) was aseptically transferred to a 50 ml polypropylene tube. Prepared ground beef extracts (10 ml; spiked in with *E. coli* 25922, *S. typhimurium* 14028, *P. aeruginosa* 27853, *P. aeruginosa* 9027, *S. auerus* 25923, *S. epidermidis* 12228 or *L. monocytogenes* 13932)) was combined with 5 g of XAD-4 hydrophobic resin for 30 minutes at room temperature and rotated at 25 rpm. The resin was separated from the sample by allowing the resin to settle and then removing or decanting the supernatant free of resin into a tube used for staining. Alternatively, after the incubation of the sample with resin, the supernatant was poured through a filter (i.e. a BD Falcon™ Cell Strainer (40 μm)) into the tube used for staining. Falcon™ is a trademark of Becton, Dickinson and Company.

Staining Resin-Treated Sample and FACS Analysis

The extracts from the resin-treated samples were fluorescently stained using 0.5 mM EDTA, 20 mM HEPES, 1:100 stock of nucleic acid dye stain (e.g., SYTO® 13 by Invitrogen) for 15 minutes at room temperature. Two minutes prior to the completion of the staining, 10% nitrazine yellow was added. The resin treated sample was then analyzed by flow cytometry in a Becton Dickinson FACSCalibur™ flow cytometer using a standard protocol. Other identical samples which were not combined with the resin were also stained and used as a control.

Results

Figure 2:
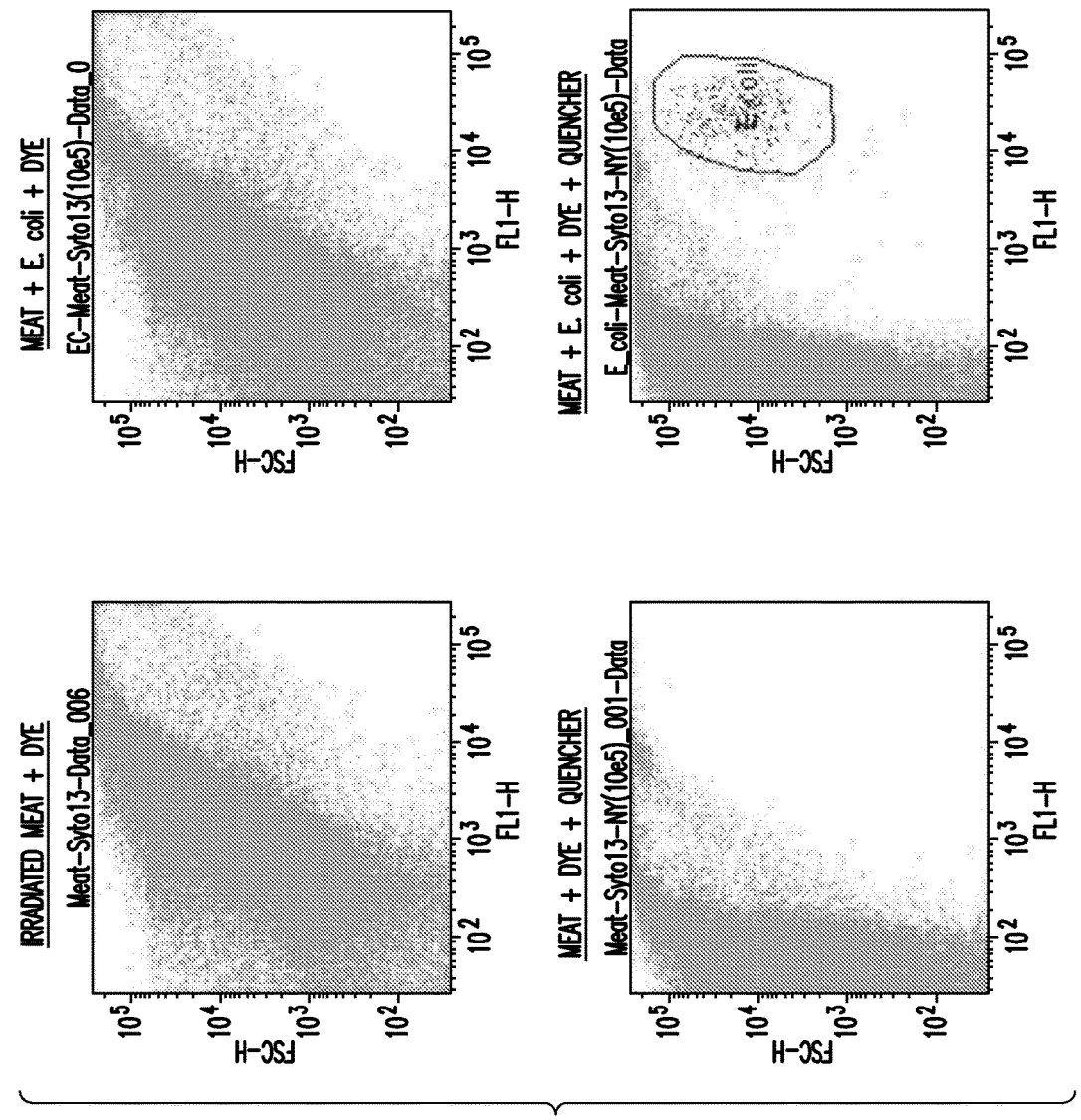
FIG. 2 presents a series of dot plots generated during the flow cytometric analysis to detect the presence or absence of *E. coli* in a biological sample comparing results for samples treated with resin with samples not treated with resin.
Figure 3:
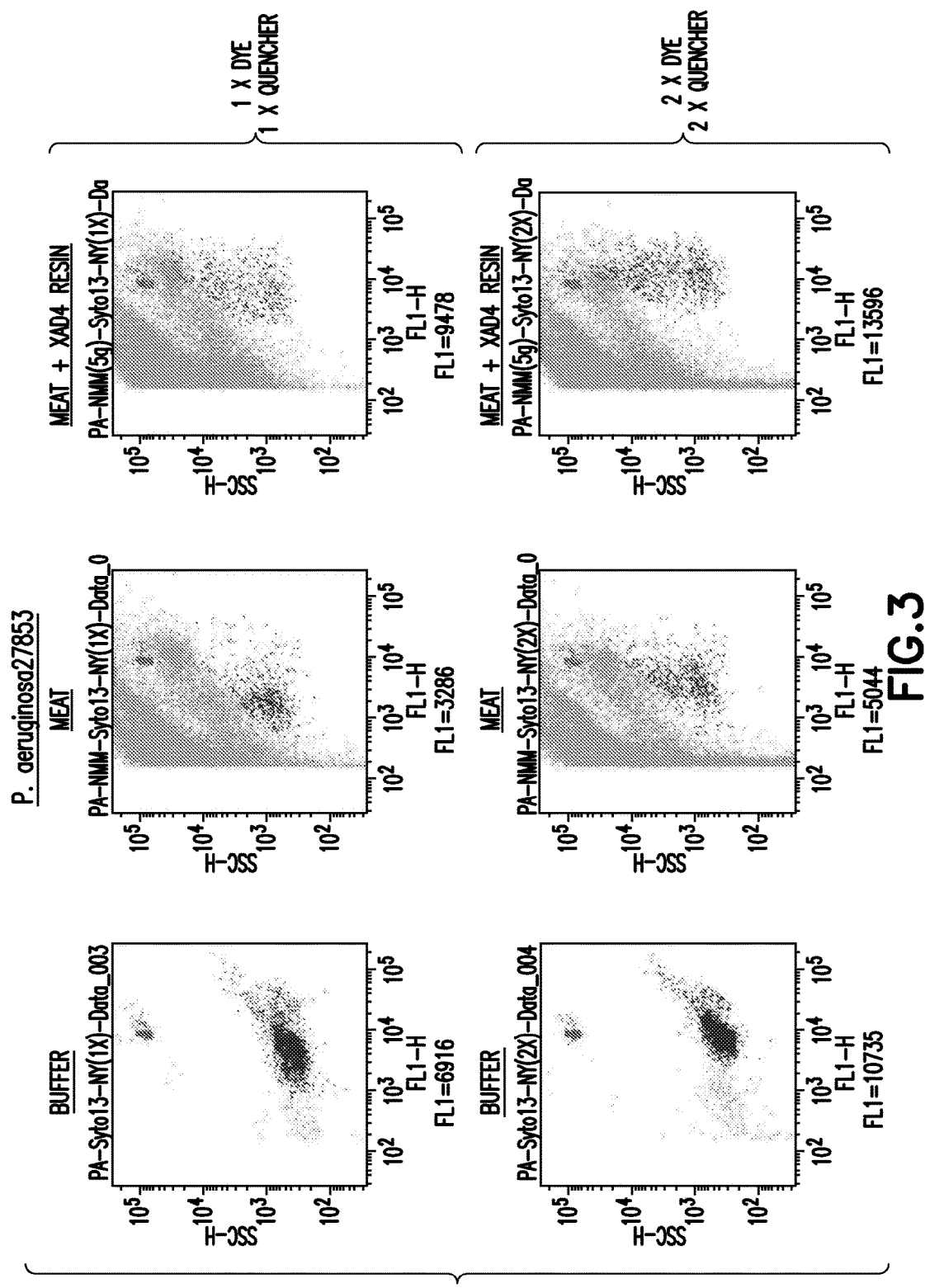
FIG. 3 presents a series of dot plots generated during the flow cytometric analysis to detect the presence or absence of *P. aeruginosa* in a biological sample comparing results for samples treated with resin with samples not treated with resin.

After the resin and quencher treatment, the fluorescent intensities increased 17%, 76%, 174% and 108% for *E. coli*, *S. typhimurium*, *P. aeruginosa* 27853 and *P. aeruginosa* 9027, respectively, compared to the samples that were not treated with resin. (See FIGS. 2 and 3). Flow cytometry results correlated well with colony counting results for all bacteria tested. See FIG. 4. For example, *P. aeruginosa* sample treated with resin yielded $8.1 \times 10^4$ cfu/ml by flow cytometry and $8.7 \times 10^4$ cfu/ml by colony count. The sample of *P. aeruginosa* that was not treated with resin yielded $4.9 \times 10^4$ cfu/ml on flow cytometry and $1.1 \times 10^5$ cfu/ml for colony count. This result, which was obtained from the information in FIG. 3 (FL1=5044) shows that sample not treated with resin failed to correlate with the colony count measurements. Based on the results from the untreated sample, there appears to be unacceptably high interference from the complex matrix particles resulting in low detectable signal.

Due to the presence of the resin, the overall fluorescent staining intensities of Gram-positive bacteria was slightly lower than the staining intensities for Gram-positive bacteria in the absence of the resin (between 3.4% and 9.7%). Nonetheless, because of the high fluorescent staining intensities of the three Gram-positive strains tested (*S. aureus*, *S. epidermidis*, and *L. monocytogenes*), the lower staining intensity had no impact on bacteria counting accuracy and sensitivity.

A small amount of fluorescent bacteria-like particles in the resin-treated unspiked beef samples were also observed, which was considered to be mere background.

The resin was observed to remove interference and provide samples that yielded higher fluorescent signals for some bacterial populations without a significant loss of bacteria in the samples (e.g., less than 30% less bacterial populations on the resin-treated samples compared to amounts that are projected by calculation to exist in the sample based upon amounts of bacteria actually added to sample (i.e. the calculation is based on sample spiked with a known quantity of bacteria).

The whole procedure required only 30 minutes of incubation with resin at room temperature, followed by a simple separation step. Since the flow cytometer is likely to be clogged by the complex matrices (e.g., meat particles), a filtration step after the resin treatment does not add an additional step since such a step is required even without the resin treatment. By removing the interfering particles from the samples, affinity agents to isolate microorganisms from other sample constituents were no longer necessary.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of analyzing a biological or environmental sample for the presence or absence of at least one target microorganism, comprising:
   obtaining a sample to be tested for the presence or absence of the at least one target microorganism;
   preparing the sample;
   combining the sample with a resin selected to bind to non-target particles in the sample;
   removing the resin from the sample, the resin carrying the non-target particles therewith;
   combining the sample with a nucleic acids stain after removing the resin therefrom, wherein the nucleic acid stain permeates and labels the target microorganism; and
   analyzing the stained sample comprising the labeled target microorganism.

2. The method of claim 1 wherein the biological or environmental sample is derived from a cosmetic comprising a complex matrix.

3. The method of claim 1, wherein the biological or environmental sample is derived from a soil sample comprising a complex matrix.

4. The method of claim 1, wherein the biological or environmental sample is derived from a food product selected from the group consisting of meat, milk, eggs, butter, and water, wherein the food product comprises a complex matrix.

5. The method of claim 1 wherein the resin is selected from a group consisting of hydrophobic resin, a polyaromatic resin, and a porous resin.

6. The method of claim 1 wherein the resin is a non-functional polymeric resin adsorbent.

7. The method of claim 1 wherein the sample and resin are incubated at room temperature.

8. The method of claim 1 wherein the nucleic acid stain label is a fluorescent label.

9. The method of claim 1 wherein the sample is analyzed using a flow cytometer.

10. The method of claim 1 further comprising adding a quencher to the biological sample, wherein the quencher is selected to suppress unwanted fluorescence.

11. An assay for a biological or environmental sample to determine the presence, absence or amount of viable microorganisms in the sample, comprising:
    obtaining a biological sample to be assayed for the presence or absence of target viable microorganisms;
    preparing the biological sample by adding a resin to the biological sample, the resin selected to bind to non-target particles in the sample;
    removing the resin from the sample, the resin carrying non-target particles therewith;
    adding to the sample a background signal-reducing substance comprising molecule that will bind to non-target particles in the sample;
    adding a nucleic acid stain that permeates and labels viable cells to the biological sample; and
    analyzing the stained biological sample;
    wherein the background signal-reducing molecules do not significantly permeate the target viable microorganisms and bind to the non-target particles in a similar manner and with a similar efficiency as the nucleic acid stain, and
    wherein the nucleic acid stains are added sequentially or simultaneously with the background signal-reducing molecules.

12. The assay of claim 11, wherein the biological or environmental sample is derived from a food product, a cosmetic, a soil sample, or water, and wherein the sample comprises a complex matrix.

13. The assay of claim 11, wherein the resin is selected from a group consisting of hydrophobic resin, a polyaromatic resin, and a porous resin.

14. The assay of claim 11, wherein the resin is a non-functional polymeric resin adsorbent.

15. The assay of claim 11, wherein the sample is analyzed using a flow cytometer.

16. The assay of claim 11, wherein the nucleic acid stain label is a fluorescent label.

17. An assay for a biological or environmental sample to determine the presence, absence or amount of viable microorganisms in the sample, comprising:
    obtaining a sample to be assayed for the presence or absence of target viable microorganisms;
    preparing the biological sample by adding a resin to the biological sample, the resin selected to bind to non-target particles in the sample;
    removing the resin from the sample, the resin carrying non-target particles therewith;
    adding to the sample background signal-reducing substance comprising molecules that will bind to non-target particles in the sample;
    adding a nucleic acid stain that permeates and labels viable cells to the sample; and
    analyzing the stained biological sample;
    wherein the background signal-reducing molecules added to the sample are covalently linked to fluorescent quenchers, the fluorescent quenchers quench the fluorescent signal of the nucleic acid dye by spectra overlap, the background signal-reducing molecules bind to the non-target particles in a similar manner and with a similar efficiency as the nucleic acid stains and, the background signal-reducing molecules do not permeate target viable microorganisms, and
    wherein the nucleic acid stains are added sequentially or simultaneously with the background signal-reducing molecules.

18. The assay of claim 17, wherein the biological or environmental sample is derived from a food product, a cosmetic, a soil sample, or water, and wherein the sample comprises a complex matrix.

19. The assay of claim 17, wherein the resin is selected from a group consisting of hydrophobic resin, a polyaromatic resin, and a porous resin.

20. The assay of claim 17, wherein the resin is a non-functional polymeric resin adsorbent.

21. The assay of claim 17, wherein the sample is analyzed using a flow cytometer.

22. The assay of claim 17, wherein the nucleic acid stain label is a fluorescent label.

* * * * *